United States Patent [19]

Wolfrum et al.

[11] B 4,013,631

[45] Mar. 22, 1977

[54] MONOAZO DYESTUFFS CONTAINING AN N-β-1,2,3-TRIAZOLYLETHYL ANILINO COUPLING COMPONENT

[75] Inventors: Gerhard Wolfrum, Opladen; Heinrich Gold, Cologne-Stammheim, both of Germany

[73] Assignee: Bayer Aktiengesellschaft, Leverkusen, Germany

[22] Filed: Nov. 1, 1966

[21] Appl. No.: 591,141

[44] Published under the second Trial Voluntary Protest Program on March 23, 1976 as document No. B 591,141.

[30] Foreign Application Priority Data

Nov. 8, 1965   Germany .............................. 47620

[52] U.S. Cl. ..................................... 260/157; 8/26; 8/27; 8/41 A; 260/154; 260/155; 260/156; 260/158; 260/162; 260/308 A
[51] Int. Cl. ....................... C09b 29/36; D06p 1/08
[58] Field of Search ................... 260/157, 158, 146

*Primary Examiner*—Floyd D. Higel
*Attorney, Agent, or Firm*—Plumley and Tyner

[57] ABSTRACT

Azo dyestuffs of the formula

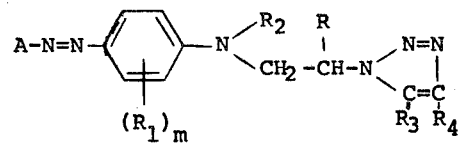

wherein A stands for the residue of the diazo component, R stands for hydrogen or methyl, $R_1$ is a non-ionic substituent, M is a number from 0 to 2, $R_2$ stands for hydrogen or for an aliphatic, araliphatic, or aromatic radical, $R_3$ and $R_4$ are independently selected from the group consisting of hydrogen, alkyl, alkoxy methyl, aryl, carboxy, carboalkoxy, said dyestuff being free of sulphonic acid groups and being adapted for use in dyeing and printing synthetic fiber materials. The quaternary salts of the dyestuffs are also adapted for use in such dyeing and printing.

11 Claims, No Drawings

MONOAZO DYESTUFFS CONTAINING AN N-β-1,2,3-TRIAZOLYLETHYL ANILINO COUPLING COMPONENT

The invention relates to valuable new azo dyestuffs which are free from sulphonic acid groups and correspond to the general formula

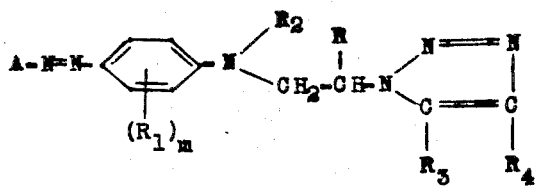

(I)

and to their water-soluble quaternary salts of the general formula

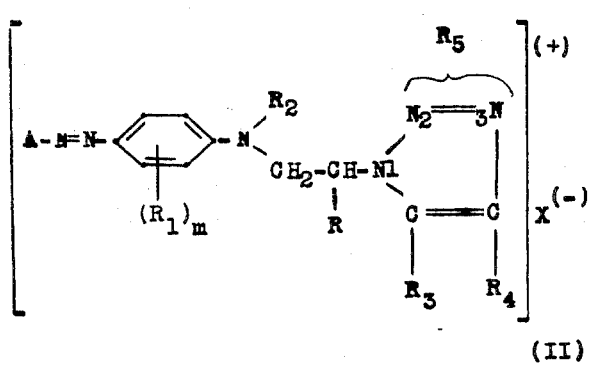

(II)

In the formulae (I) and (II) the symbol A denotes the radical of a diazo component, R is hydrogen or —CH$_3$, R$_1$ is a non-ionic substituent, R$_2$ is hydrogen, an aliphatic, araliphatic or aromatic radical, R$_3$ and R$_4$ are hydrogen or the same or different alkyl radicals, aryl, alkoxy-methyl, carboxylic acid or carbalkoxy radicals, R$_5$ is an alkyl or benzyl radical; the alkyl radicals in the aforesaid groups preferably contain 1 – 4 carbon atoms; m stands for the number 0, 1 or 2, and X$^-$ for an anion. The radical A of the diazo component is preferably a carbocyclic radical, such as a radical of the benzene series, or a heterocyclic radical, and the aryl radicals R$_3$ or R$_4$ are preferably phenyl, chlorophenyl, bromophenyl or alkyl (1 – 4 carbon atoms)-phenyl radicals.

Among the non-ionic substituents R$_1$, halogen, such as —Cl or —Br, lower alkyl radicals, such as methyl, ethyl and propyl radicals, trifluoroalkyl, lower alkoxy radicals, such as methoxy and ethoxy radicals, and thioether radicals should be specially mentioned; the alkyl radicals preferably contain 1 – 4 carbon atoms.

The radical R$_2$ may contain further substituents, for example, a cyano group in the β-position of an ethyl radical or a carbalkoxy group also in the β-position of an ethyl radical.

It has not yet unequivocally been established whether the alkyl or benzyl radical R$_5$ stands in the 2- or 3-position of the triazole ring of the dyestuffs of the general formula (II). It is highly probable that the radical R$_5$ is attached to the nitrogen atom 3 of the triazole ring.

The new azo dyestuffs of the formula (I) are prepared by combining the diazonium compound of an amine of the formula

A — NH$_2$      (III)

in which A has the same meaning as above, with a coupling component of the general formula

(IV)

in which R, R$_1$, R$_2$, R$_3$, R$_4$ and m have the same meaning as above, the starting components being free from sulphonic acid groups.

The quaternary salts of the new azo dyestuffs, which correspond to the general formula (II), are prepared, for example, by combining the diazonium compound of an amine of the formula

A — NH$_2$      (III)

in which A has the same meaning as above, with a coupling component of the formula

(V)

in which R, $R_1$, $R_2$, $R_3$, $R_4$, $R_5$, $m$ and $X^-$ have the same meaning as above, the starting components being free from sulphonic acid groups.

Quaternary salts of the general formula (II) in which A denotes the radical of a carbocyclic diazo component, can also be prepared by treating azo dyestuffs which are free from sulphonic acid groups and correspond to the general formula

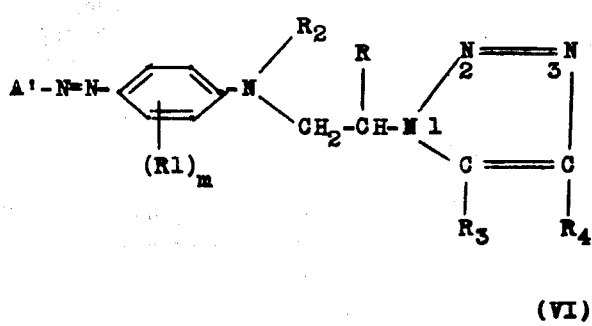

(VI)

in which R, $R_1$, $R_2$, $R_3$, $R_4$ and $m$ have the same meaning as above and A′ stands for a radical of the benzene series, with alkylating agents $R_5X$, with quaternisation of the triazole ring. It has not yet unequivocally been established whether in this process the alkyl or benzyl radical $R_5$ becomes attached to the nitrogen atom 2 or 3 of the triazole ring of the dyestuffs of the general formula (VI), but it is highly probable that the radical $R_5$ becomes attached to the nitrogen atom 3 of the traizole ring.

The coupling components to be used according to the present process are novel. They are N-alkyl-N- β-[1,2,3-triazolyl-(1)]-ethyl or -propyl -anilines and their non-ionic substitution products and their quaternary salts. These compounds are obtained, for example, when N-alkyl-N-β-chloroethyl or N-alkyl-N-β-chloropropyl-anilines are reacted with inorganic azides, such as sodium azide, in an aqueous or aqueous-alcoholic solution to form N-alkyl-N-β-azidoethyl- or N-alkyl-N-β-azidopropyl-anilines and these are reacted in a further step with (optionally substituted) acetylene to form the triazoles-(1,2,3) of the general formula (IV). The quaternary salts of the formula (V) are formed therefrom by alkylation. The following compounds may be used as alkylating agents, for example: methyl chloride, methyl bromide, methyl iodide, benzyl chloride, trimethyl-oxonium-boron fluoride, dimethyl sulphate, diethyl sulphate, ethyl bromide, p-toluene-sulphonic acid methyl, ethyl or butyl ester.

Suitable coupling components for the synthesis of the new dyestuffs are, for example: N-methyl-N-{β-[1,2,3,-triazolyl-(1)]-ethyl}-aniline, N-ethyl-N-{β-[1,2,3-triazolyl-(1)]-ethyl}-aniline, N-propyl-N-{β-[1,2,3-triazolyl-(1)]-ethyl}-aniline, N-butyl-N-{β-[1,2,3-triazolyl-(1)]-ethyl}-aniline, N-β-cyano-ethyl-N-{β-[1,2,3-triazolyl-(1)]-ethyl}-aniline, N-β-ethoxy-carbonylethyl-N-{β-[1,2,3-triazolyl-(1)]-ethyl}-aniline, N-methyl-N-{β-[1,2,3-triazolyl-(1)]-propyl}-aniline, N-ethyl-N-{β-[1,2,3-triazolyl-(1)]-propyl}-aniline, N-butyl-N-{β-[1,2,3-triazolyl-(1)]-propyl}-aniline, N-ethyl-N-{β-[1,2,3-triazolyl-(1)]-ethyl}-3-methyl-aniline, N-β-cyanoethyl-N-{β-[1,2,3-triazolyl-(1)]-ethyl}-3-methylaniline, N-ethyl-N-{β-[1,2,3-triazolyl-(1)]-propyl}-3-methyl-aniline, N-ethyl-N-{β-[1,2,3-triazolyl-(1)]-ethyl}-3-ethyl-aniline, N-ethyl-N-{β-[1,2,3-triazolyl-(1)]-ethyl}-3-chloro-aniline, N-β-cyanoethyl-N-{β-[1,2,3-triazolyl-(1)]-ethyl}-3-chloro-aniline, N-β-ethoxy-carbonylethyl-N-{β-[1,2,3-triazolyl-(1)]-ethyl}-3-chloro-aniline, N-ethyl-N-{β-[1,2,3-triazolyl-(1)]-propyl}-3-chloro-aniline, N-ethyl-N-{β-[1,2,3-triazolyl-(1)]-ethyl}-3-methoxyaniline, N-butyl-N-{β-[1,2,3-triazolyl-(1)]-ethyl}-3-methoxyaniline, N-β-cyanoethyl-N-{β-[1,2,3-triazolyl-(1)]-ethyl}-3-methoxyaniline, N-ethyl-N-{β-[1,2,3-triazolyl-(1)]-propyl}-3-methoxyaniline, N-ethyl-N-{β-[1,2,3-triazolyl-(1)]-ethyl}-3-ethoxyaniline, N-ethyl-N-{β-[1,2,3-triazolyl-(1)]-ethyl}-3-acetylamino-aniline, N-ethyl-N-{β-[1,2,3-triazolyl-(1)]-propyl}-3-acetylaminoaniline, N-ethyl-N-{β-[1,2,3-triazolyl-(1)]-ethyl}-2-methoxyaniline, N-ethyl-N-{β-[1,2,3-triazolyl-(1)]-ethyl}-2-methoxy-5-acetylaminoaniline and the quaternary salts of these compounds which contain the alkyl or benzyl group attached to the nitrogen atom 2 or 3 of the triazole ring.

Suitable diazo components A—$NH_2$ are, for example: aniline, 2-chloroaniline, 3-chloroaniline, 4-chloroaniline, 2-methyl-aniline, 3-methylaniline, 4-methylaniline, 2-ethylaniline, 3-ethylaniline, 4-ethylaniline, 2-nitroaniline, 3-nitroaniline, 4-nitroaniline, 2-chloro-4-nitroaniline, 2-chloro-3-nitroaniline, 2-chloro-4,6-dinitroaniline, 2-nitro-4-chloroaniline, 2-nitro-3-chloroaniline, 2,4-dinitroaniline, 2,6-dichloro-4-nitroaniline, 2-cyano-4-nitroaniline, 2,4-dicyanoaniline, 2,3-dichloroaniline, 2,4-dichloroaniline, 3,5-dichloroaniline, 3,4-dichloroaniline, 2,4,5-trichloroaniline, pentachloroaniline, 2-chloro-4-methylaniline, 2-methyl-4-chloro-aniline, 4-aminobenzoic acid, 4-aminobenzoic acid ethyl ester, 3-nitro-4-amino-benzoic acid, 3-nitro-4-amino-benzoic acid ethyl ester, 2-amino-benzoic acid, 3-chloro-4-cyanoaniline, 3-chloro-6-cyanoaniline, 4-aminobenzoic acid amide, 4-aminobenzoic acid dimethylamide, 4-methyl-sulphonyl aniline, 2-trifluoromethyl-4-methyl-sulphonylaniline, 2-ethyl-sulphonyl-4-nitroaniline, 2-chloro-4-ethyl-sulphonylaniline, 4-methoxyaniline, 3-methoxyaniline, 2-nitro-4-methoxyaniline, 2-methoxy-4-nitroaniline, 2-aminothiazole-(1,3), 2-amino-5-nitro-thiazole-(1,3), 2-amino-benzothiazole-(1,3), 2-amino-6-ethoxy-benzothiazole-(1,3), 5-amino-3-phenyl-thiadiazole-(1,2,4), 3-aminopyridine, 8-aminoquinoline, 3-aminoindazole, 3-amino-triazole-(1,2,4).

Coupling of the starting components is carried out in known manner, for example, in a neutral or weakly to strongly acidic aqueous medium.

If the dyestuffs according to the invention are prepared by alkylation of dyestuffs of the general formula (VI), the alkylation is expediently carried out by heating in inert organic solvent, for example, in hydrocarbons, such as benzene, toluene, or xylene; halogenated hydrocarbons, such as carbon tetrachloride, tetrachloroethane, chloroform, chlorobenzene, o-dichlorobenzene; nitrated hydrocarbons, such as nitrobenzene, or nitronaphthalene; or in dimethyl formamide, acetonitrile or dimethyl sulphoxide with the use of, preferably, equivalent amounts of alkylating agents, for example, methyl chloride, methyl bromide, methyl iodide, ethyl bromide, benzyl chloride, trimethyl-oxonium-boron fluoride, dimethyl sulphate, diethyl sulphate, p-toluene-sulphonic acid methyl, ethyl or butyl ester.

The resultant quaternised dyestuffs are sparingly soluble in the solvents used and can be isolated by filtering off. If dimethyl formamide, acetonitrile or dimethyl sulphoxide is used and the quaternised dyestuffs remain partially or completely dissolved, they can be separated by dilution with water and addition of water-soluble salts, for example, sodium or potassium chloride.

The dyestuffs of the formula (II) prepared by coupling diazonium compounds of amines of the formula (III) with the coupling components of the formula (V), as well as those prepared by alkylating the dyestuffs of the formula (VI) can be purified by dissolving them in water and separating them by the addition of water-soluble salts, for example, sodium or potassium chloride.

The dyestuffs obtained according to the present process contain the anionic radical $X^-$ which preferably is the radical of a strong acid, for example, of sulphuric acid, or its semiesters, or of an aryl-sulphonic acid, or a halogen ion. These ions can be replaced, however, with the radicals of other acids, for example, of phosphoric acid, hydrofluoboric acid, formic acid, acetic acid, tartaric acid, lactic acid. The dyestuff salts can also be converted into double salts by means of inorganic salts, for example, zinc chloride.

The water-insoluble dyestuffs of the general formula (I) obtained according to the present process are suitable for the dyeing and printing of fully synthetic fibres, especially those of polyamides, cellulose esters and polyesters, in particular, polyterephthalic acid glycol esters. The dyeings have good fastness properties. The dyestuffs of the general formula (II) obtained according to the invention are water-soluble and eminently suitable for the dyeing and printing of fully synthetic fibres of polymers and copolymers of acrylonitrile and dicyanoethylene, fast shades being obtained. These dyestuffs can also be used for the dyeing and printing of tanned cellulose materials, silk and leather.

In the following Examples which are given for the purpose of illustrating the invention, the parts are parts be weight. The quaternary substituent in the triazolium dyestuff is uniformly shown in the 3-position of the triazole ring, although this position has not yet been unequivocally established by experiment.

EXAMPLE 1

16.2 Parts 2,4-dichloroaniline are dissolved in water containing 25 parts concentrated hydrochloric acid and diazotised at 0°– 5°C. with a solution of 6.9 parts sodium nitrite in 25 parts water. After filtration, this diazonium salt solution is added to a solution of 21.6 parts of the coupling component of the formula

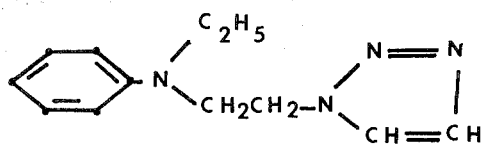

in 200 parts 5% hydrochloric acid and the coupling which sets in immediately is completed after some time by the addition of sodium acetate. When the coupling is completed, the resultant dyestuff is washed with water until free from salt and dried. 37.1 Parts of a yellow-orange powder are obtained. This dyestuff of the formula

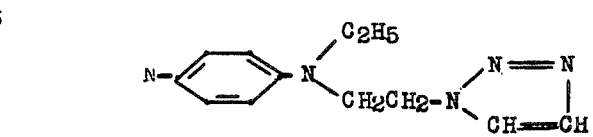

dyes fibres and fabrics of polyamides in reddish yellow shades of good general fastness properties.

The coupling component used in this Example is prepared as follows: N-ethyl-N-β-chloroethyl-aniline is reacted in an aqueous-ethanolic medium with sodium azide to form N-ethyl-Nβ-azidoethyl-aniline, and acetylene is added on to this azide.

The N-ethyl-N-{β-[1,2,3-triazolyl-(1)]-ethyl}-aniline is a colourless compound which boils at 153°C. under a pressure of 0.05 mm. Hg. and has melting point 48° – 49°C.

Other valuable dyestuffs which are obtained by combining the coupling component of Example 1 1 the specified diazo components, are compiled in Table I. 1.

Table 1

| Example | Diazo component | Coupling component | Shade on Polyamide |
|---|---|---|---|
| 2 | 3,b-dichloroaniline | as in Example 1 | reddish yellow |
| 3 | 3,4-dichloroaniline | '' | '' |
| 4 | 2,4,5-trichloroaniline | '' | '' |
| 5 | Pentachloroaniline | '' | strongly reddish yellow |
| 6 | 2-cyano-5-chloroaniline | '' | '' |
| 7 | 2,4-dicyanoaniline | '' | red |
| 8 | 3,4-dicyanoaniline | '' | strongly yellowish red |
| 9 | 4-aminobenzoic acid ethyl ester | '' | reddish yellow |
| 10 | 6-ethoxy-2-aminobenzothiazole-(1,3) | '' | scarlet |

Table 1-continued

| Example | Diazo component | Coupling component | Shade on Polyamide |
|---|---|---|---|
| 11 | 3-phenyl-5-amino-1,2,4-thiadiazole | " | " |
| 12 | 2-trifluoromethyl-4-chloro-aniline | " | yellowish orange |

EXAMPLE 13

The diazonium salt solution prepared according to Example 1 from 16.2 parts 2,4-dichloroaniline is added to a solution of 23 parts of the coupling component of boiling point 155°C. at 0.03 mm. Hg. and melting point 40° – 41°C.

Other valuable dyestuffs which are obtained by combining the coupling component of Example 13 with the specified daizo components, are compiled in Table 2.

Table 2

| Example | Diazo component | Coupling component | Shade on Polyamide |
|---|---|---|---|
| 14 | 3,5-dichloroaniline | as in Example 13 | strongly reddish yellow |
| 15 | 3,4-dichloroaniline | " | " |
| 16 | 2,4,5-trichloroaniline | " | " |
| 17 | Pentachloroaniline | " | yellowish orange |
| 18 | 2-cyano-5-chloroaniline | " | " |
| 19 | 2,4-dicyanoaniline | " | red |
| 20 | 3,4-dicyanoaniline | " | scarlet |
| 21 | 4-aminobenzoic acid ethyl ester | " | reddish yellow |
| 22 | 6-ethoxy-2-aminobenzothiazole-(1,3) | " | red |
| 23 | 3-phenyl-5-amino-1,2,4-thiadiazole | " | red |
| 24 | 2-trifluoromethyl-4-chloro-aniline | " | orange | the formula

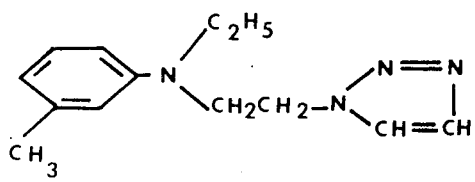

in 200 parts 5% hydrochloric acid and the coupling which sets in immediately is completed after some time by the addition of sodium acetate.

The dyestuff which is isolated in analogy with the instructions of Example 1 corresponds to the formula

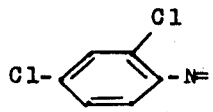

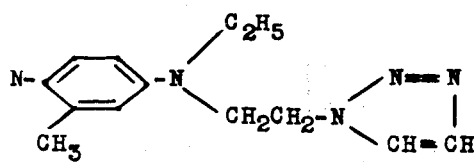

and is an orange-red powder after drying. The yield amounts to 38.7 parts. The dyestuff dyes polyamide fibres in strongly reddish yellow shades of good fastness to wet processing and light.

The coupling component used in this Example is prepared in analogy with that of Example 1 from N-ethyl-N-β-chloroethyl-m-toluidine. The compound has

EXAMPLE 25

17.3 Parts 2-chloro-4-nitroaniline are stirred at room temperature for 4 – 5 hours with a mixture of 80 parts concentrated hydrochloric acid and 20 parts water and diazotised, after the addition of 200 parts ice, at 0° – 3°C. with a solution of 6.9 parts sodium nitrite in 20 parts water. The diazonium salt solution is filtered and then added to a solution of 21.6 parts of the azo component of the formula

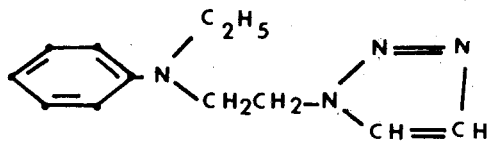

in 200 parts 5% hydrochloric acid. The coupling giving the azo dyestuff sets in immediately and is completed by the addition of sodium acetate. The resultant dyestuff is isolated by filtering off, washed with water and dried. The dyestuff corresponds to the formula

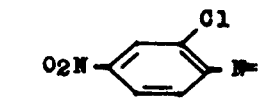

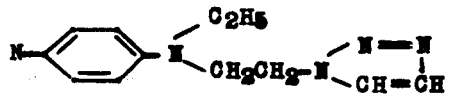

After drying, there are obtained 38.6 parts of a red-brown powder which is ground in a ball mill for 24 hours, together with 24 parts of a condensation product obtained from β-naphthalene-sulphonic acid and formaldehyde and with 35 – 70 parts water. The paste is subsequently dried in a vacuum at below 50°C and the residue is finely ground.

When applied under the usual dyeing conditions (100°C., addition of a carrier), the dyestuff so obtained yields on fibres of polyterephthalic acid glycol ester a yellowish red dyeing of good fastness properties.

The coupling component of Example 25 was prepared by reaction of the sulphuric acid semi-ester (or its sodium salt) of N-ethyl-N-β-hydroxyethyl-aniline with sodium azide to form N-ethyl-N-β-azido-ethylaniline in a two-phase aqueous organic solvent system, for example in water/chlorobenzene, and reaction of the azido compound thus obtained with acetylene.

Other valuable dyestuffs which are obtained by combining the specified diazo components with the stated azo components to form the monoazo dyestuffs are compiled in Table 3.

Table 3

| Example | Diazo component | Coupling component | Shade on Polyester |
|---|---|---|---|
| 26 | 2-cyano-4-nitroaniline | 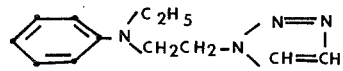 | bluish red |
| 27 | 2,4-dicyanoaniline | " | ruby |
| 28 | 3,4-dicyanoaniline | " | reddish orange |
| 29 | 2,6-dichloro-4-nitroaniline | " | yellow brown |
| 30 | 2-nitro-4-ethoxyaniline | " | yellowish orange |
| 31 | 2-nitroaniline | " | yellow |
| 32 | 2,4-dinitroaniline | " | strongly reddish yellow |
| 33 | 2-aminobenzene-sulphonic acid phenyl ester | " | yellow |
| 34 | 2-bromo-4-methyl-sulphonylaniline | " | reddish yellow |
| 35 | 4-methyl-sulphonylaniline | " | yellow |
| 36 | 5-trifluoromethyl-2-ethyl-sulphonylaniline | 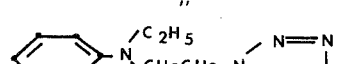 | reddish yellow |
| 37 | pentachloroaniline | " | " |
| 38 | 6-ethoxy-2-amino-benzothiazole-(1,3) | " | strongly yellowish red |
| 39 | 5-nitro-2-aminothiazole-(1,3) | " | violet |
| 40 | 2-cyano-4-nitroaniline | 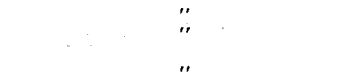 | bluish ruby |
| 41 | 2,4-dicyanoaniline | " | bluish Bordeaux |
| 42 | 3,4-dicyanoaniline | " | strongly reddish orange |
| 43 | 2,6-dichloro-4-nitroaniline | " | red-brown |
| 44 | 2-nitro-4-ethoxyaniline | " | orange |
| 45 | 2-nitroaniline | " | somewhat reddish yellow |
| 46 | 2,4-dinitroaniline | " | yellowish orange |
| 47 | 2-aminobenzenesulphonic acid phenyl ester | " | reddish yellow |
| 48 | 2-bromo-4-methyl-sulphonylaniline | " | strongly reddish yellow |
| 49 | 4-methyl-sulphonylaniline | " | reddish yellow |
| 50 | 5-trifluoromethyl-2-ethyl-sulphonylaniline | " | yellowish orange |
| 51 | pentachloroaniline | " | yellowish orange |
| 52 | 6-ethoxy-2-aminobenzothiazole-(1,3) | " | scarlet |
| 53 | 5-nitro-2-aminothiazole-(1,3) | " | blue-violet |
| 54 | 2-chloro-4-nitroaniline | " | red |

| | | | Shade on polyamide |
|---|---|---|---|
| 55 | 2,4-dichloroaniline | 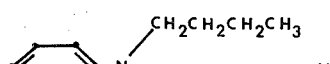 | strongly reddish yellow |
| 56 | 3,4-dichloroaniline | 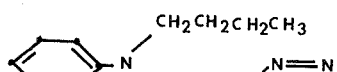 | strongly reddish yellow |

Table 3-continued

| Example | Diazo component | Coupling component | Shade on Polyester |
|---|---|---|---|
| 57 | 3,4-dicyanoaniline | '' | yellowish scarlet |
| 58 | 6-ethoxy-2-aminobenzothiazole-(1,3) | '' | scarlet |

The coupling component used in Examples 55 – 58 is a slightly yellow-coloured oil of boiling point 175°C. at 0.1 mm. Hg.

EXAMPLE 59

A diazonium salt solution prepared from 17.3 parts 2-chloro-4-nitroaniline is combined exactly according to the instructions of Example 25 with 21.6 parts of the azo component of Example 25 to form the dyestuff of the formula

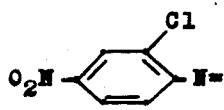

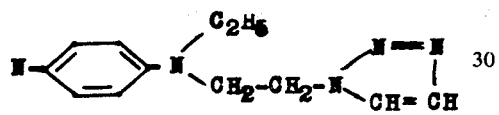

and the dyestuff thus prepared is dried at 80°C. for several hours. 39 Parts of the completely anhydrous dyestuff are obtained in the form of a brown-red powder.

This dyestuff is finely pulverised and introduced with stirring into 300 parts anhydrous o-dichlorobenzene. The resultant suspension is heated to 100°C. while stirring, whereupon the dyestuff dissolves almost completely. 12.5 Parts dimethyl sulphate are then added dropwise at 100°C. within 30 minutes. The temperature is subsequently raised to 120°C. and stirring is continued at this temperature for 2 hours. A substantial part of the quaternised dyestuff separates already during this operation. The mixture is then cooled to 5° – 10°C. and the crystallised dyestuff is filtered off.

The dyestuff is washed twice with o-dichlorobenzene on a suction filter and then dried. After drying, there are obtained 50.1 parts of a red-brown, very readily water-soluble dyestuff of the probable formula

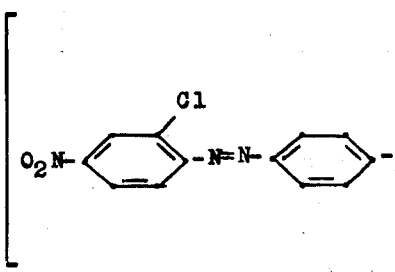

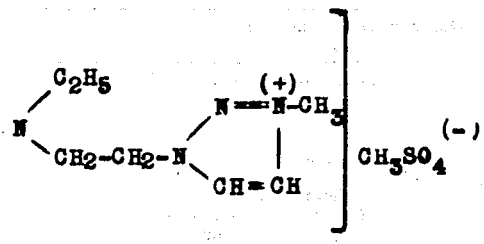

This dyestuff dyes fibres or fabrics of polyacrylonitrile from a weakly acidic bath under the usual dyeing conditions in red shades of excellent fastness properties.

The dyestuff of this Example is also characterised in that it is eminently suitable for combination with other cationic dyestuffs. For example, in a grey mixture prepared from this dyestuff together with the two dyestuffs

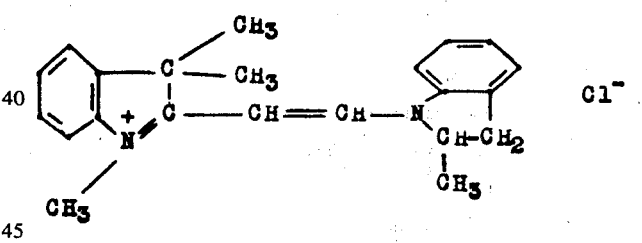

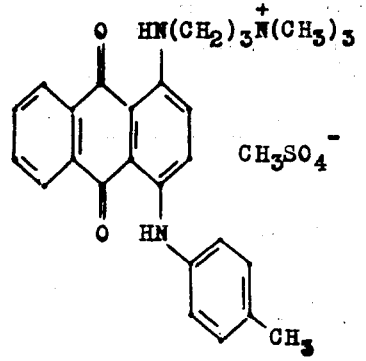

the dyestuff of Example 59 draws on the polyacrylonitrile fibre completely level with the two other dyestuffs.

EXAMPLE 60

The diazonium salt solution prepared according to Example 25 from 17.3 parts 2-chloro-4-nitro-aniline is added at 0°C., while stirring, to a solution of 34.8 parts of the azo component of the formula

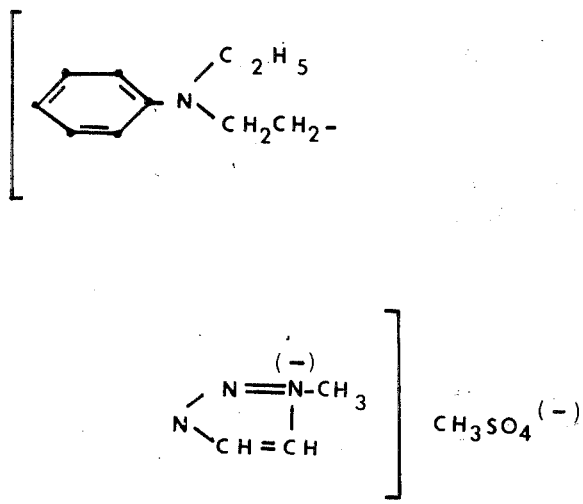

in 350 parts water. The coupling to form the azo dyestuff is completed by the addition of sodium acetate. The resultant azo dyestuff is completely separated by the addition of 30 – 45 parts sodium chloride and filtered off. It is dissolved in 400 parts water at 70°C. while still moist, the solution is filtered while hot and the dyestuff is separated from the filtrate by the addition of 30 – 40 parts sodium chloride. The dyestuff is filtered off and dried at 60°C. 43.2 Parts of a red-brown, very readily water-soluble dyestuff of the probable formula

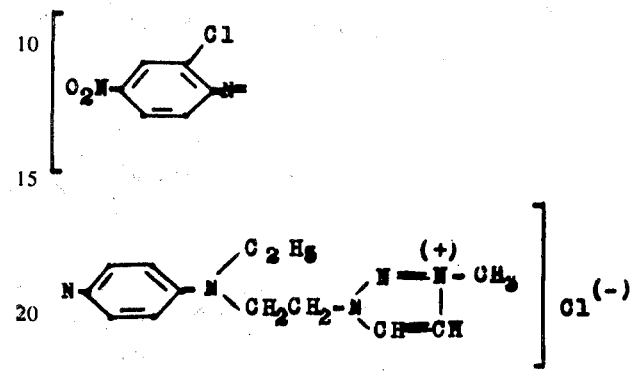

are obtained.

(During working up, at least the major part of the original methosulphate anion is replaced by the chloride anion).

The dyestuff so prepared contains the same dyestuff cation as the dyestuff of Example 59 prepared in a different way; it also dyes polyacrylonitrile fibres in red shades of excellent fastness properties.

The coupling component used in this Example was prepared from N-ethyl-N-{β-[1,2,3-triazolyl-(1)]-ethyl}-aniline and dimethyl sulphate in o-dichlorobenzene at 110° – 120°C. The compound was used for coupling in the form of an oily crude product after distilling off the o-dichlorobenzene.

Other dyestuffs which are obtained by reacting the specified azo dyestuff with the stated alkylating agent in xylene or o-dichlorobenzene at 100° – 120°C., are compiled in the following Table 4.

Table 4

| Example | Azo dyestuff | Alkylating agent | Shade on polyacrylonitrile |
|---|---|---|---|
| 61 |  | dimethyl sulphate | reddish Bordeaux |
| 62 | 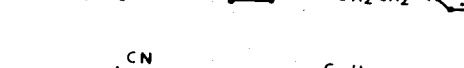 | diethyl sulphate | bluish Bordeaux |
| 63 | 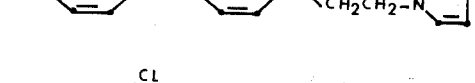 | p-toluene-sulphonic acid methyl ester | brownish orange |
| 64 | 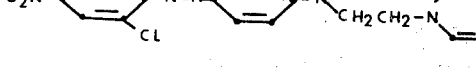 | dimethyl sulphate | yellowish red |

Table 4-continued

| Example | Azo dyestuff | Alkylating agent | Shade on polyacrylonitrile |
|---|---|---|---|
| 65 | 2-CN, 4-Cl-C₆H₃-N=N-C₆H₄-N(C₂H₅)(CH₂CH₂-1,2,3-triazol-1-yl) | ethyl bromide | reddish yellow |
| 66 | 4-HOOC, 3-NO₂-C₆H₃-N=N-C₆H₄-N(C₂H₅)(CH₂CH₂-1,2,3-triazol-1-yl) | dimethyl sulphate | yellowish red |
| 67 | 4-O₂N, 2-Cl-C₆H₃-N=N-(3-CH₃-C₆H₃)-N(C₂H₅)(CH₂CH₂-1,2,3-triazol-1-yl) | p-toluene-sulphonic acid ethyl ester | red-Bordeaux |
| 68 | 4-O₂N, 2-CN-C₆H₃-N=N-(3-CH₃-C₆H₃)-N(C₂H₅)(CH₂CH₂-1,2,3-triazol-1-yl) | ethyl iodide | bluish Bordeaux |
| 69 | 2-CN, 4-Cl-C₆H₃-N=N-(3-CH₃-C₆H₃)-N(C₂H₅)(CH₂CH₂-1,2,3-triazol-1-yl) | dimethyl sulphate | reddish orange |
| 70 | 4-O₂N, 2,6-Cl₂-C₆H₂-N=N-(3-CH₃-C₆H₃)-N(C₂H₅)(CH₂CH₂-1,2,3-triazol-1-yl) | " | strongly brownish red |
| 71 | 4-O₂N, 2-Cl-C₆H₃-N=N-C₆H₄-N(CH₃)(CH₂CH₂-1,2,3-triazol-1-yl) | " | red |
| 72 | 4-O₂N, 2-Cl-C₆H₃-N=N-C₆H₄-N(CH₂CH₂CH₂CH₃)(CH₂CH₂-1,2,3-triazol-1-yl) | " | red |
| 73 | 4-O₂N, 2-Cl-C₆H₃-N=N-(3-Cl-C₆H₃)-N(C₂H₅)(CH₂CH₂-1,2,3-triazol-1-yl) | " | scarlet |
| 74 | 4-O₂N, 2-Cl-C₆H₃-N=N-(3-OCH₃-C₆H₃)-N(C₂H₅)(CH₂CH₂-1,2,3-triazol-1-yl) | " | Bordeaux |

Table 4-continued

| Example | Azo dyestuff | Alkylating agent | Shade on polyacrylonitrile |
|---|---|---|---|
| 75 | O₂N—C₆H₃(Cl)—N=N—C₆H₃(NHCOCH₃)—N(C₂H₅)—CH₂CH₂—N(N=N triazole) | " | bluish red |
| 76 | O₂N—C₆H₃(Cl)—N=N—C₆H₃(OCH₃)—N(C₂H₅)—CH₂CH₂—N(N=N triazole) | " | yellowish red |
| 77 | O₂N—C₆H₃(Cl)—N=N—C₆H₄—N(CH₂CH₂CN)(CH₂CH₂—N triazole) | " | yellowish red |
| 78 | O₂N—C₆H₃(Cl)—N=N—C₆H₄—N(C₂H₅)—CH₂CH₂—N(N=N, C=C(COOC₂H₅)₂) | diethyl sulphate | red |
| 79 | O₂N—C₆H₃(Cl)—N=N—C₆H₃(CH₃)—N(C₂H₅)—CH₂CH₂—N(N=N, CH₂OCH₃, CH₂OCH₃) | dimethyl sulphate | reddish Bordeaux |
| 80 | O₂N—C₆H₃(Cl)—N=N—C₆H₃(CH₃)—N(C₂H₅)—CH₂CH₂—N(N=N, CH=C—C₆H₅) | " | reddish Bordeaux |
| 81 | O₂N—C₆H₃(Cl)—N=N—C₆H₃(CH₃)—N(C₂H₅)—CH₂—CH(CH₃)—N(N=N triazole) | " | red-Bordeaux |

Other valuable dyestuffs which are obtained by combining the diazonium compounds of the specified amines with the stated coupling components are compiled in the following Table 5.

Table 5

| Example | Diazo component | Coupling component | Shade on polyacrylonitrile |
|---|---|---|---|
| 82 | 2-aminobenzothiazole-(1,3) | 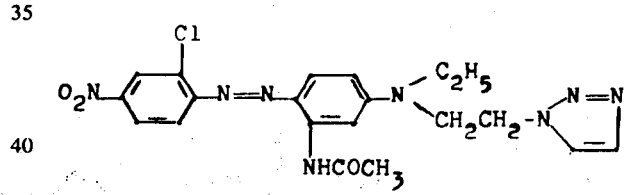 | yellowish red |
| 83 | 2-amino-6-ethoxy-benzothiazole-(1,3) | " | red |
| 84 | 2-aminothiazole-(1,3) | " | yellowish red |
| 85 | 2-amino-5-nitrothiazole-(1,3) | " | violet |
| 86 | 5-amino-3-phenyl-thiadiazole-(1,2,4) | " | red |
| 87 | 2-amino-6-ethoxy-benzothiazole-(1,3) | | bluish red |
| 88 | 2-amino-6-chlorobenzo-thiazole-(1,3) | " | bluish red |
| 89 | 3-aminotriazole-(1,2,4) | " | reddish yellow |

EXAMPLE 90

The diazonium salt solution prepared according to Example 25 from 17.3 parts of 2-chloro-4-nitro-aniline is added to a solution of 27.5 parts of the azo component of the formula

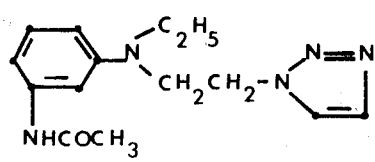

in 250 parts of acetic acid. The coupling to form the azo dyestuff is completed by the addition of sodium acetate. The resultant azo dyestuff is isolated by filtration, washed salt-free and acid-free and dried. One obtains 42.1 parts of a dyestuff of the following constitution This dyestuff dyes fibres from polyterephthalic acid glycol esters somewhat bluish red shades with excellent fastness to wet processing and thermofixation.

The azo component used in Example 90 was prepared from the azo component of Example 1 by nitration in concentrated sulphuric acid with nitrating acid, reduction of the nitro group to the amino compound and acetylation of the amino compound with acetic anhydride or acetyl chloride.

In Table 6 there are listed other valuable dyestuffs which are obtained by combining the following diazo and azo components to the monoazo dyestuffs:

Table 6

| Example | Diazo component | Azo component | Shade on polyester |
|---|---|---|---|
| 91 | 2-cyano-4-nitro-aniline | as in Example 90 | red-violet |
| 92 | 3-phenyl-5-amino-1,2,4-thiadiazole | as in Example 90 | clear red |
| 93 | 2-bromo-4,6-di-nitro-aniline | as in Example 90 | strongly bluish Bordeaux |
| 94 | 3-phenyl-5-amino-1,2,4-thiadiazole | 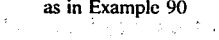 | scarlet |

Table 6-continued

| Example | Diazo component | Azo component | Shade on polyester |
|---------|-----------------|---------------|---------------------|
| 95 | 2-bromo-4,6-di-nitro-aniline | " | Bordeaux |
| 96 | 2-bromo-4,6-di-nitro-aniline | (structure) | bluish Bordeaux |
| 97 | 2-bromo-4,6-di-nitro-aniline | (structure) | blue |
| 98 | 2-chloro-4-nitro-aniline | (structure) | red |
| 99 | 3-aminobenzene-sulphonic acid-β-hydroxyethyl-amide | (structure) | Shade on polyamide reddish yellow |
| 100 | 4-chloro-3-amino-benzene-sulphonic acid-β-hydroxy-ethylamide | " | Shade on polyamide yellowish orange |

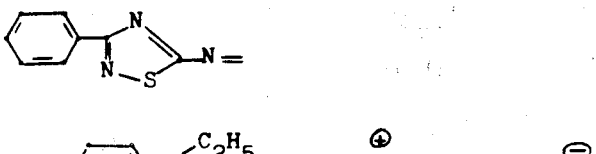

We claim:
1. An azo dyestuff selected from the group consisting of

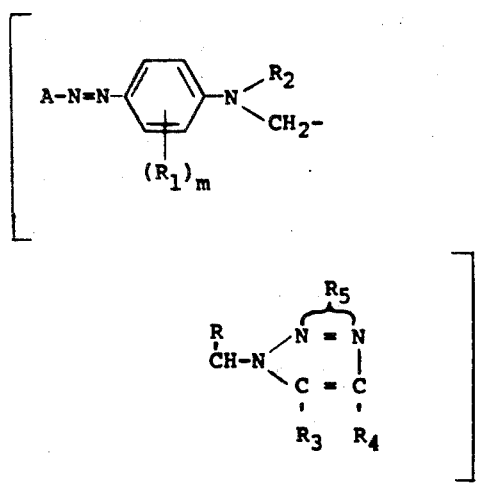

and

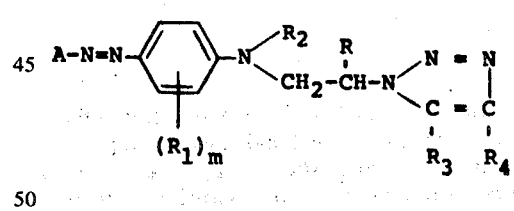

wherein R stands for hydrogen or methyl; $R_1$ is a member selected from the group consisting of chloro, bromo, lower alkyl, trifluoro lower alkyl, lower alkoxy, and acetylamino; m is an integer from 0 to 2; $R_2$ stands for hydrogen, lower alkyl, or substituted lower alkyl, wherein the substituents are selected from the group consisting of cyano and ethoxy carbonyl; $R_3$ and $R_4$ are independently selected from the group consisting of hydrogen, lower alkyl, lower alkoxy methyl, phenyl, chlorophenyl, bromophenyl, lower alkyl phenyl, carboxylic acid, carbolower alkoxy; $R_3$ is selected from the group consisting of lower alkyl and benzyl; A is selected from the group consisting of phenyl, substituted phenyl, thiazol (1,3)-2-yl, 5-nitro thiazol (1,3)-2-yl, benzothiazol (1,3)-2-yl, 6-chloro benzothiazol (1,3)-2-yl, 6-ethoxy benzothiazol (1,3)-2-yl, 3-phenyl-thiadiazole (1,2,4)-5-yl, pyridin-3-yl, quinolin-8-yl, indazol-3-yl, and triazol (1,2,4)-3-yl, wherein the substituents on said phenyl radical are members of the group consisting of halogen, lower alkyl, lower alkoxy, nitro, cyano, carboxy, trifluoromethyl, carboxy lower alkyl, sulphoxy lower alkyl, carbonamide, lower alkyl carbonamide, dilower alkyl carbonamide, sulfonamide, lower alkyl sulfonamide, and dilower alkyl sulfonamide; X stands for an anion; and wherein the alkyl groups contain from 1–4 carbon atoms; said dyestuff being free of sulphonic acid groups.

2. An azo dyestuff of claim 1 of the formula

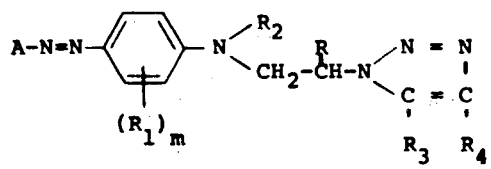

3. An azo dyestuff of claim 1 of the formula

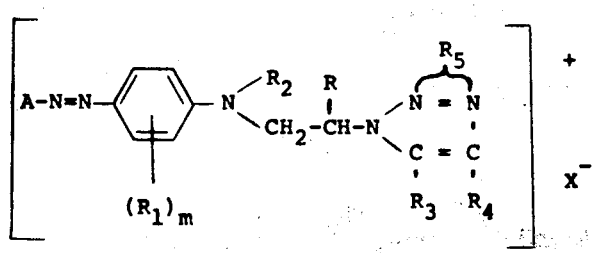

4. A dyestuff of claim 2 wherein A is selected from the group consisting of phenyl and substituted phenyl.

5. A dyestuff of claim 3 wherein A is selected from the group consisting of phenyl and substituted phenyl.

6. A dyestuff of claim 2 corresponding to the formula

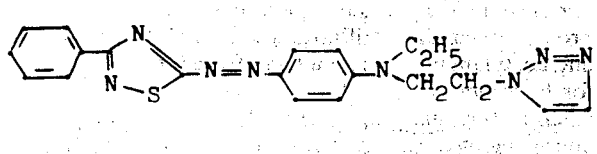

7. A dyestuff of claim 4 corresponding to the formula

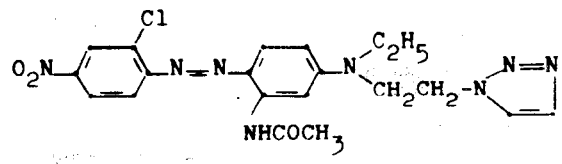

8. A dyestuff of claim 2 corresponding to the formula

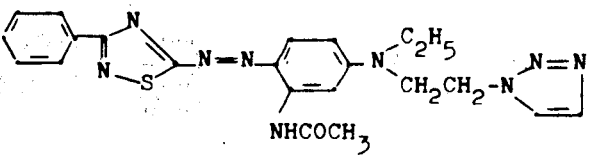

9. A dyestuff of claim 5 corresponding to the formula

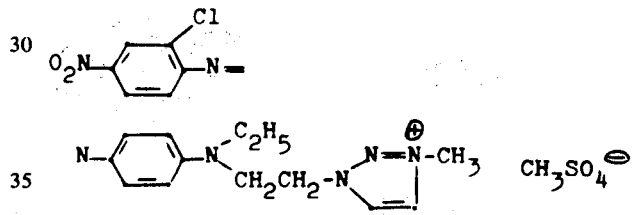

10. A dyestuff of claim 5 corresponding to the formula

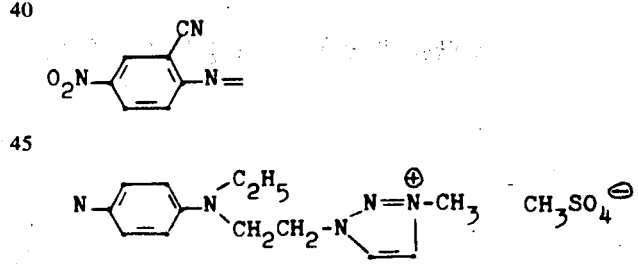

11. A dyestuff of claim 3 corresponding to the formula